United States Patent [19]
Barnes et al.

[11] Patent Number: 5,379,764
[45] Date of Patent: Jan. 10, 1995

[54] NON-INVASIVE DETERMINATION OF ANALYTE CONCENTRATION IN BODY OF MAMMALS

[75] Inventors: Russell H. Barnes; Jimmie W. Brasch, Sr., both of Columbus, Ohio; David L. Purdy, Marion Center, Pa.; William D. Lougheed, Toronto, Canada

[73] Assignee: Diasense, Inc., Pittsburgh, Pa.

[21] Appl. No.: 987,766

[22] Filed: Dec. 9, 1992

[51] Int. Cl.$^6$ ................................................ A61B 5/00
[52] U.S. Cl. .................................... 128/633; 128/664; 356/39
[58] Field of Search ................................ 128/633–635, 128/664–665, 666–667; 356/39–41

[56] References Cited

U.S. PATENT DOCUMENTS

| | | | |
|---|---|---|---|
| 3,958,560 | 5/1976 | March . | |
| 3,973,118 | 8/1976 | La Montaigne | 250/226 |
| 4,014,321 | 3/1978 | March . | |
| 4,102,646 | 7/1978 | Sleeter | 23/230 R |
| 4,169,676 | 10/1979 | Kaiser | 356/39 |
| 4,260,262 | 4/1981 | Webster | 356/418 |
| 4,404,642 | 9/1983 | Rosenthal | 364/571 |
| 4,427,889 | 1/1984 | Muller | 250/339 |
| 4,509,522 | 4/1985 | Manuccia et al. | 128/634 |
| 4,642,778 | 2/1987 | Hieftje et al. | 364/498 |
| 4,655,225 | 4/1987 | Dahne et al. | 128/633 |
| 4,798,954 | 1/1989 | Stevenson | 250/341 |
| 4,800,279 | 1/1989 | Hieftje et al. | 250/339 |
| 4,801,805 | 1/1989 | Butler et al. | 250/343 |
| 4,882,492 | 11/1989 | Schlager | 250/346 |
| 4,883,953 | 11/1989 | Koashi et al. | 250/226 |
| 4,975,581 | 12/1990 | Robinson et al. | 250/339 |
| 5,009,230 | 4/1991 | Hutchinson | 128/633 |
| 5,028,787 | 7/1991 | Rosenthal et al. | 250/341 |
| 5,054,487 | 10/1991 | Clarke | 128/633 |
| 5,068,536 | 11/1991 | Rosenthal | 250/341 |
| 5,070,874 | 12/1991 | Barnes et al. | 128/664 |
| 5,077,476 | 12/1991 | Rosenthal | 250/341 |
| 5,086,229 | 2/1992 | Rosenthal et al. | 250/341 |
| 5,222,495 | 6/1993 | Clarke et al. | 128/633 |

FOREIGN PATENT DOCUMENTS

| | | |
|---|---|---|
| 0160768 | 11/1985 | European Pat. Off. . |
| 0317121 | 5/1989 | European Pat. Off. . |
| 9111136 | 8/1991 | WIPO . |

OTHER PUBLICATIONS

J. Drennen, et al. Near-Infrared Spectrometric Determination of Hydrogen Ion, Glucose, and Human Serum Albumin in a Simulated Biological Matrix, Spectroscopy, vol. 6, No. 2, p. 28 (1990).

K. Beebe & B. Kowalski, An Introduction to Multivariate Colibration and Analysis, Anal. Chem. 1987, 59, p. 1007A.

P. Geladi & B. Kowalski, Partial Least–Squares Regression: A Tutorial, Analytical Chimica Acta, 185 (1986) 1–17.

D. L. Wetzel, Near Infrared Reflectance Analysis: Sleeper Among Spectroscopic Techniques, Analytical Chemistry, vol. 55, p. 1165A (1983).

R. D. Rosenthal, An Introduction to Near Infrared Quantitative Analysis (1978).

(List continued on next page.)

*Primary Examiner*—Angela D. Sykes
*Attorney, Agent, or Firm*—William H. Murray; Robert E. Rosenthal

[57] ABSTRACT

A method of non-invasive determination of the concentration of at least one analyte in the blood of a mammal, includes the steps of projecting near-infrared radiation on a portion of the body of the mammal, the radiation including a plurality of wavelengths; sensing the resulting radiation emitted from the portion of the body; deriving from the sensed resulting radiation emitted from the portion of the body a first expression for the magnitude of the sensed radiation as a function of wavelength of the sensed radiation; pretreating the first expression to minimize the influence of offset and drift to obtain a second expression for the magnitude of the sensed radiation as a function of wavelength; and performing multivariate analysis of the second expression to obtain a value for the concentration of the analyte.

8 Claims, 11 Drawing Sheets

OTHER PUBLICATIONS

N. Wang, et al., Determination of neodymium in rare earth mixtures by fourth-derivative spectrophotometry, Analytica Chimica Acta, 2541 (1991) 153–157.

C. E. Miller & B. E. Eichinger, Analysis of Rigid Polyurethane Foams by Near-Infrared Diffuse Reflectance Spectroscopy, Applied Spectroscopy, vol. 44, No. 5, p. 887 (1990).

T. Isaksson & T. Naes, Selection of Samples in Near-Infrared Spectroscopy, Part II: Selection Based on Spectral Measurements, Applied Spectroscopy, vol. 44, No. 7, p. 1152 (1990).

N. Kaiser, Laser Absorption Spectroscopy with an ATR Prism-Noninvasive in Vivo Determination of Glucose, in Feedback-controlled and preprogrammed insulin infusion in diabetes mellifus: Workshop Schloss Reisenburg 1978 (1979), at 30.

A. Miller, In Vivo Measurement of Glucose Concentrations with Lasers, in Feedback-controlled and preprogrammed insulin infusion in diabetes mellitus: Workshop held at Schloss Reisenburg 1978 (1979) at p. 33.

D. Haaland, Quantitative Infrared Analysis of Borophosphosilicate Films Using Multivariate Statistical Methods, Analytical Chemistry, 1988, 60, 1208.

D. Haaland & E. Thomas, Outlier Detection During Multivariate Quantative Analyses of Spectroscopic Data.

D. Haaland & E. Thomas, Partial Least-Squares Methods for Spectral Analyses, 1. Relation to other Quantitative Calibration Methods and the Extraction of Qualitative Information, Analytical Chemistry, 1988, 60, 1193.

D. Haaland & E. Thomas, Partial Least-Squares Methods for Spectra Analyses. 2. Application to Simulated and Glass Spectral Data, Analytical Chemistry, 1988, 60, 1202.

E. Thomas and D. Haaland, Comparison of Multivariate Calibration Methods for Quantitative Spectral Analysis, Analytical Chemistry, 1990, 62, 1091.

W. Lindberg & J. A. Persson, Partial Least-Squares Method for Spectrofluorimetric Analysis of Mixtures of Humic Acid and Lignin Sulforate, Analytic Chemistry, 1983, 55, 643.

H. Zeller, et al., Blood Glucose Measurement by Infrared Spectroscopy, The International Journal of Artificial Organs, vol. 12, No. 2, 1969, p. 129.

E. Penchant, C. Sulles & R. Jensen, Determination of Serum Cholesterol by Near-Infrared Reflectance Spectrometry, Anal. Chem. 1987, 59, 1816.

I Yoshiya, et al., Spectrophotometric monitoring of arterial oxygen saturation in the fingertip, Med. & Biol. Eng. & Comput., 1980, 18, 27–32.

M. Martens & H. Martens, Near-Infrared Reflectance Determination of Sensory Quality of Peas, Applied Spectroscopy, vol. 40, p. 303 (1985).

B. Bauer & T. Floyd, Monitoring of Glucose in Biological Fluids by Fourier Transform Infrared Spectrometry with a Cylindrical Internal Reflectance Cell, Analytical Chimica Acta, 197 (1987) 295–301.

NON-INVASIVE DETERMINATION OF ANALYTE CONCENTRATION IN BODY OF MAMMALS

BACKGROUND OF THE INVENTION

Applicants herein are the inventors of U.S. Pat. No. 5,070,874, issued Dec. 10, 1991, for "Non-invasive Determination of Glucose Concentration in Body of Patient."

This invention relates to the determination of the concentration of analytes in the body of a mammal, and in particular to the determination of the concentration of glucose in the blood of a patient who is suspected of suffering from diabetes or to control the treatment or medication of patients who already suffer from diabetes. It has particular relationship to such determination without drawing blood from the patient, i.e., by a non-invasive process and by non-invasive means.

There is widespread demand for non-invasive determination of glucose in patients. In the United States there are approximately ten million diabetics. Two million of these are Type 1 Diabetics, whose pancreas secretes no insulin; and eight million of these are Type 2 Diabetics, whose pancreas secretes insufficient insulin or secretes it too late. Most of the Type 2 Diabetics can be controlled with proper diet and weight control. Some of the Type 2 Diabetics and all of the Type 1 Diabetics require one or more shots of insulin per day. Insulin controls the body's utilization of glucose or sugar in the blood and, in the correct concentrations, prevents hyperglycemia (excess glucose) which, if left uncorrected, can lead to ketosis, coma and death. Glucose determination is also indispensable for sufferers from hypoglycemia who must ingest glucose containing fluids, such as orange juice, if the glucose in their blood decreases to a low level.

Hyperglycemia in the diabetic is strongly suspected of being responsible for the long-term effects of diabetes which include heart disease, arteriosclerosis, blindness, stroke, hypertension, kidney failure, and premature death. Severe hypoglycemia has similar drastic consequences. In a normal person, the blood glucose level may vary between 60 and 130 milligrams per deciliter, a variance exceeding 100%; whereas, in a diabetic, the levels may vary from time to time from 40 to 500 milligrams per deciliter, a variance of 1150% for hyperglycemia. For hypoglycemia, 60 milligrams per deciliter indicates that treatment is necessary; the glucose may reach a dangerous level of 20 milligrams per deciliter. These large swings of glucose levels must be avoided to prevent the symptoms and complications of the disease. To avoid the swings, the diabetic must be able to conveniently monitor his blood glucose level, and then vary his caloric intake, diet and insulin to control the level. For effective control, frequent blood glucose monitoring is necessary.

The only practicable, reliable method currently available for monitoring blood glucose is by means of blood sampling. The diabetic pricks his epidermis with a needle or lance, usually in the finger, draws a drop of blood, and absorbs the blood on a chemically treated strip of paper. He can then read the glucose level by placing the strip in a glucometer (a spectrophotometer which reads glucose concentrations); or he can compare the color change of the strip with a calibrated color chart. The direct reading instruments are more accurate. Other methods include measuring the electrical resistance of the strip with a glucometer which is an ohmmeter calibrated in milligrams per deciliter. For effective control, some diabetics must utilize a finger prick four or more times a day.

It is desirable to dispense with the drawing and analyzing of blood and it is an object of this invention to achieve this purpose, providing for effective non-invasive determination of analyte concentration in the body of a mammal, and in particular glucose concentration in a patient suspected to suffer from, or already suffering from, diabetes.

European Publication 0 160 768, dated Nov. 13, 1985, to Clause Dahne and Daniel Cross, discloses one prior art technique for the non-invasive determination of glucose concentration. In Dahne, a beam of radiation in selected bands, 1575, 1765, 2100 and 2270±15 nanometers is impinged on a portion of the patient's body, penetrating into the portion, and the radiation resulting from the reaction within the body on the incident radiation is analyzed photometrically for the presence quantitatively of glucose. The resulting radiation which is analyzed may be scattered radiation or the transmitted radiation which, in effect, is the incident radiation less the predominant fraction of the scattered radiation and the radiation absorbed by the portion of the body.

Dahne suffers from the disadvantage that its process lacks the precision demanded for the effective monitoring of glucose concentration. The range of concentration over which the glucose is in practice monitored for effective control of the patient is between 40 and 500 milligrams per deciliter, but even lower concentrations may be encountered in hyperglycemia or hypoglycemia. A concentration appreciably greater than 120 milligrams per deciliter indicates a diabetic condition and treatment by diet or insulin. In the actual practice of Dahne's process, the highest concentration of glucose which was measured was one molar (1M) and the lowest concentration of glucose which was measured was 0.05 molar (page 18). The chemical formula for glucose is $C_6H_{12}O_6$. In a 1M solution of glucose, there are 180.16 grams per liter or 18,000 milligrams per deciliter. In 0.05 mole, there are 0.9 grams or 900 milligrams per deciliter. This is far out of the range of glucose concentrations which must be measured for effective control and, indeed, out of the range which is compatible with life. There is no evidence in Dahne that its process is more effective than is indicated by its tests.

It is accordingly an object of this invention to overcome the disadvantages and drawbacks of the prior art and to provide for the precise effective non-invasive determination of the concentration of blood analytes in a mammal, and particularly glucose in a human patient, taking into consideration the concentrations actually involved in such determination.

SUMMARY OF THE INVENTION

This invention arises from the realization that in any expression, for example, in a graph, of the concentration of glucose in blood as a function of the wavelengths over which an analysis is carried out, the measure of the maximum concentration, which must be precisely determined, is often obscured by the presence of other chemical species. It has been realized in arriving at this invention that the specific spectral features associated with species which must be measured may be emphasized and readily determined by appropriate mathematical techniques. In particular, such mathematical techniques may involve a step of pretreatment, followed by a step of multivariate analysis. The step of pretreatment serves to eliminate or minimize the effects of detector offset and optical scattering drift. In particular, the step of pretreatment may also include deriving a new function, the nth derivative with respect to wavelength of the expression defining the concentration of glucose as a function of wavelength, over a defined region of this nth derivative. The nth derivative with respect to wavelength is then used as an input for multivariate analysis. Using multivariate analysis techniques, the glucose concentration is then determined. As is conventional in the use of multivariate techniques in chemical analysis, the multivariate analysis uses a model developed by comparing predicted concentrations of the species to be measured in specimens to the known concentrations of the species in that specimen.

Specifically, the non-invasive measurement of the concentration of glucose in blood is performed with a near-infrared radiation source, a probe, a spectrum analyzer with a detector and a data processor. The probe may include a dual fiber-optic conductor of near infrared radiation which is used in either the transmission or scattering mode. Radiation from the near infrared source is transmitted through one of the dual conductors, the end of which is placed near or in contact with a portion of the patient's body. The radiation transmitted into the body undergoes scattering and characteristic absorption depending on the identity of the species present. A portion of the radiation having undergone scattering and absorption is back scattered from the body and collected and transmitted back to the spectral analyzer/detector system by the other fiber-optic conductor, which is referred to as the sensing or pick-up conductor. The end of the sensing or pick-up fiber-optic conductor, placed near or in contact with the body, is arranged so that either a transmission or a scattering measurement is performed. In the transmission mode, the end of the pick-up fiber-optic conductor is arranged so that the near infrared radiation from the source can be passed through the portion of the body, which may be the ear lobe, tongue or webbing between the fingers or toes, and its spectral absorption characteristics measured. This is accomplished by placing the body section between the ends of the dual conductor so that radiation from the fiber-optic conductor connected to the near infrared source passes through the body section to the pick-up fiber-optic conductor which transmits the attenuated radiation to the spectral analyzer/detector. In the scattering mode, a bifurcated fiberoptic probe is preferably used. The bifurcated probe includes two separate bundles of fibers, one bundle being connected to the near infrared source, and the other bundle being connected to the spectral analyzer/detector system. The pick-up bundle may be, for example, centrally located and the source conductor bundle may be disposed in any configuration surrounding the central bundle. Alternatively, individual pick-up fibers may be disposed at selected locations in a bundle of conductors connected to the source. To measure blood glucose, the sensing end of the probe is placed near or in direct contact with an outer surface of the body. Near infrared radiation from the fibers connected to the source is transmitted through that portion of the body undergoing both characteristic spectral absorption and scattering. Some of the scattered radiation which has traveled through the body experiencing absorption is collected by the pick-up fibers in this configuration and then transmitted to the spectrum analyzer/detector.

The spectrum analyzer for this application can include a dispersive spectrometer with a prism or diffraction grating, a spectrometer in a Czerny-Turner configuration, a set of optical filters, a scanning interferometer, a stationary interferometer, or it may include a Hadamard transform spectrometer. Hadamard transform spectroscopy is described in a paper by Hammaker et al. in *Vibrational Spectra and Structure*, Vol. 15, Nov. 1986, edited by J. R. Durig, Elsevier Press, Amsterdam, Holland. The purpose of the spectrum analyzer is to disperse the near infrared radiation passing through the body into its spectral components. Selected wavelength ranges are focused on detector cells, which provide an analog signal proportional to the intensity of radiation in the selected wavelength ranges.

The data processor receives the output signal from the spectral analyzer. This output signal may be a reflected light intensity as a function of wavelength. The reflectance, R, is given by $$R = I_0 / I$$

where $I_0$ is the intensity of the radiation incident on the portion of the patient's body and I is the resulting radiation reflected back or scattered by the portion. When the reflectance is graphically presented, the quantity log (1/R) is customarily presented and called absorbance.

The data processor then calculates the concentration of blood glucose, and formats the output to a display or recording device giving blood glucose concentration in selected units. Preferably, a microprocessor in the data processor is used to perform data processing and control the operation of the spectral analyzer.

To investigate and demonstrate the practical utility of the invention, near infrared measurements were performed in different concentrations of glucose in rabbit ears. It was found that the intensity of the reflected radiation as a function of wavelength in the near infrared band of glucose between 1100 and 1900 nm. yielded effective data from which glucose concentrations could be derived. In the practice of this invention, in its broad aspects, measurements are made over the range of wavelengths from 700 to 3000 nm.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which.

DETAILED DESCRIPTION OF A PREFERRED EMBODIMENT

Figure 1:
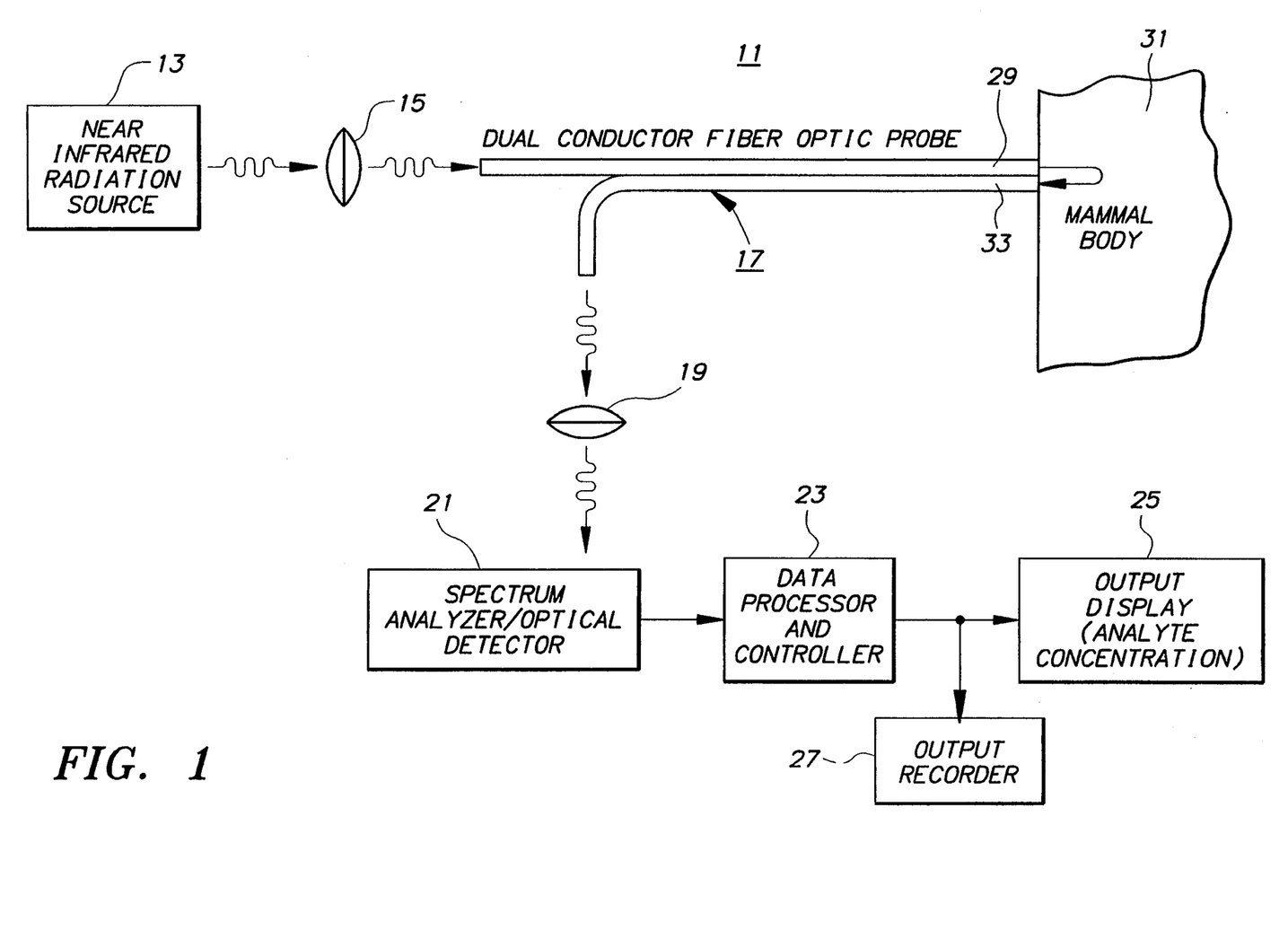
FIG. 1 is a block diagram showing an embodiment of this invention with which the method of invention is practiced.

FIG. 1 shows apparatus 11 for the non-invasive determination of the glucose concentration in a patient. This apparatus includes a source 13 of near-infrared radiation, a first lens system 15, a dual conductor fiber-optic probe 17, a second lens system 19, a spectrum analyzer/detector 21, a data processor and controller 23, an output display device 25 and an output recorder 27. As stated the source may produce radiation over the range from 700 to 3000 nm. The data presented in this application were produced using a Model 6500 System Near Infrared Spectrometer acquired from Pacific Scientific Instrument Division of Pacific Scientific, Ltd. The address of this Instrument Division is 2431 Linden Lane, Silver Spring, Md. 20910. The source may be an appropriate tungsten filament bulb, with an infrared filter disposed intermediate the bulb and the input radiation conductor 29. The intensity of the radiation of the source over the wavelengths of interest must be maintained constant. This may be achieved, for example, by thermally isolating the bulb from its surroundings and maintaining the current through the filament constant. The lens systems 15 and 19 are represented by single-lens symbols. In actual practice, they are appropriate combinations of lenses including focusing lenses and collimators on the outlet side. The fiber-optic probe 17 includes an input radiation conductor 29 for transmitting radiation to a portion 31, for example, an ear lobe or wrist, of the patient's body and pickup or sensing radiation conductor 33 for receiving the resulting radiation from the portion 31. The output end of the input conductor 29 and the input or sensing end of the pickup conductor 33 are preferably in firm contact with the outer surface of the portion 31 of the subject's body. While each conductor 29 and 33 is represented by a symbol for a single conductor, each radiation conductor, in actual practice of this invention, includes bundles of optical fibers.

Radiation from the source 13 is directed by the lens system 15 into conductor 29 and, at its outlet, is projected into the portion 31. This incident radiation induces scattered radiation within the body portion 31, some of which passes through the end of conductor 33 and through the conductor and is directed by lens system 19 into the spectrum analyzer/detector. While FIG. 1 discloses apparatus in which scattered radiation is analyzed, the analysis of transmitted radiation, i.e., the input radiation less the back scattered and absorbed radiation, plus any forward scattered radiation, is within the scope of equivalents of this invention. In this case, the ends of conductors 29 and 33, instead of being side-by-side in contact with adjacent surfaces of the body portion 31, would be in contact with the outer surfaces on opposite sides of the body portion 31, for example, with opposite surfaces of the ear lobe. The radiation, which is in this case passed through conductor 33, is predominantly the radiation from the source 13 less the radiation scattered and absorbed by the molecules of the water in the blood, the glucose and other constituents of the blood. The skin also contributes to the scattering and absorption.

With the apparatus as shown in FIG. 1, the resulting back scattered radiation emitted by the body portion 31 is passed by pickup conductor 33 and lens system 19 to the spectrum analyzer/detector 21 where this radiation is spread into a spectrum. The spectrum is focused on an array of optical detectors. A selected wavelength range is focused on each detector. For example, a range of 15 nanometers may be focused on each detector. The detectors may be lead-sulfide detectors, which are well-known in the field of infrared spectroscopy of grains and other agricultural products. Each detector converts the radiation in the corresponding selected wavelength range to electrical signals which are transmitted to the data processor 23. In a preferred embodiment, intermediate each detector and the data processor, there is a pre-amplifier, an amplifier, and an analog-to-digital converter. It should be noted that, to reduce noise effects, a chopper is preferably provided before the spectrometer to modulate the infrared beam. The amplifier is a lock-in amplifier, so that only the portion of the signal containing data is transmitted to the analog-to-digital converter.

The data processor then applies a step of pretreatment to the function of the magnitude of the radiation intensity versus wavelength. The step of pretreatment has the effect of minimizing, or eliminating the effects of detector offset and drift. In a preferred embodiment, the pretreatment step comprises taking the nth derivative, and in particular, the second derivative, of the intensity vs. wavelength function. Alternatively, the pretreatment step may comprise the steps of subtracting the mean of the whole spectrum from each data point in the spectrum and then dividing each data point by the standard deviation of the whole spectrum.

The pretreated data is then subjected to multivariate analysis. The result of the step of multivariate analysis is a glucose concentration. Various techniques of multivariate analysis are known in the chemical arts. A preferred multivariate analysis technique is partial least squares (PLS). The technique of partial least squares is taught in, for example, Geladi & Kowalski, Partial Least Squares Regression: A Tutorial, Analytica Chimica Acta, 185 (1986) 1-17. Various commercial software packages are available for implementation of the partial least squares technique. Such software packages are sold, for example, by NIR Systems, of Silver Spring, Md., under the name NSAS, (together with certain equipment), and in the Spectra Calc, Lab-Calc, and GRAMS software packages of Galactic Industries, of Salem, N.H. Other techniques such as principal component regression, principal component analysis, and multiple regression analysis (also called multiple linear regression analysis or ordinary least squares analysis) may also be used. Those skilled in the art of constructing models using these techniques will be able to do so using appropriate commercial software packages. The techniques of multiple regression analysis would ordinarily be employed if the number of data points is relatively small.

The first step in using multivariate techniques is the development of a model. The model relates various values of pretreated transmittance and reflectance with respect to wavelength to analyte concentrations. In developing the model, the device of the invention is employed to take measurements of reflected or transmitted light intensity on a subject. Simultaneously, invasive, highly-accurate methods are used to determine analyte concentrations. This process is accomplished over a range of analyte concentrations for two sets of data. One of these sets of data is the calibration set, and the other set is a prediction set.

The intensity values of the calibration set are pretreated, and are used as input for the multivariate model-developing software, together with the invasively-measured analyte concentrations. The software calculates, in the PLS technique, an initial set of factors, which make up an initial model. The initial model is then employed to obtain an analyte concentration from the prediction set infrared intensity values. This predicted value is then compared to the invasively-determined analyte concentration obtained simultaneously with the prediction set infrared intensity values. A person suitably skilled in the art of constructing PLS models then reviews and analyzes the factors of the initial model and makes appropriate adjustments, to develop an improved model. The techniques employed by a person skilled in the art of constructing multivariate statistical models are set forth in, for example, in Mark, Principles and Practice of spectroscopic Calibration (1992). After an acceptable model has been iteratively developed, the model is employed in analyzing real data to obtain analyte concentrations.

As an example, the foregoing technique was employed in developing an multivariate statistical model using data on glucose concentrations in the blood of rabbits. Infrared intensity data were obtained by performing non-invasive near-infrared reflectance, using a device according to the invention on the abdomen of a rabbit. Simultaneously with the reflectance readings, blood samples were taken, and glucose concentrations were obtained by a clinical glucose analyzer manufactured by Yellow Springs Instruments. Initially, readings were taken from the rabbit in a normal state. The rabbit then received an intravenous insulin injection, and further measurements were taken, to obtain sensed intensity values corresponding to lower glucose concentrations. The rabbit was then injected with a glucose solution, and a further set of reflectance and invasive measurements were taken, at elevated blood glucose concentrations. A final set of measurements were taken after the rabbit's blood glucose concentration had returned to normal.

Certain data obtained above were designated a calibration set, to be used in building the PLS model. Other readings were designated a prediction set, to be used for testing the model.

Figure 2:
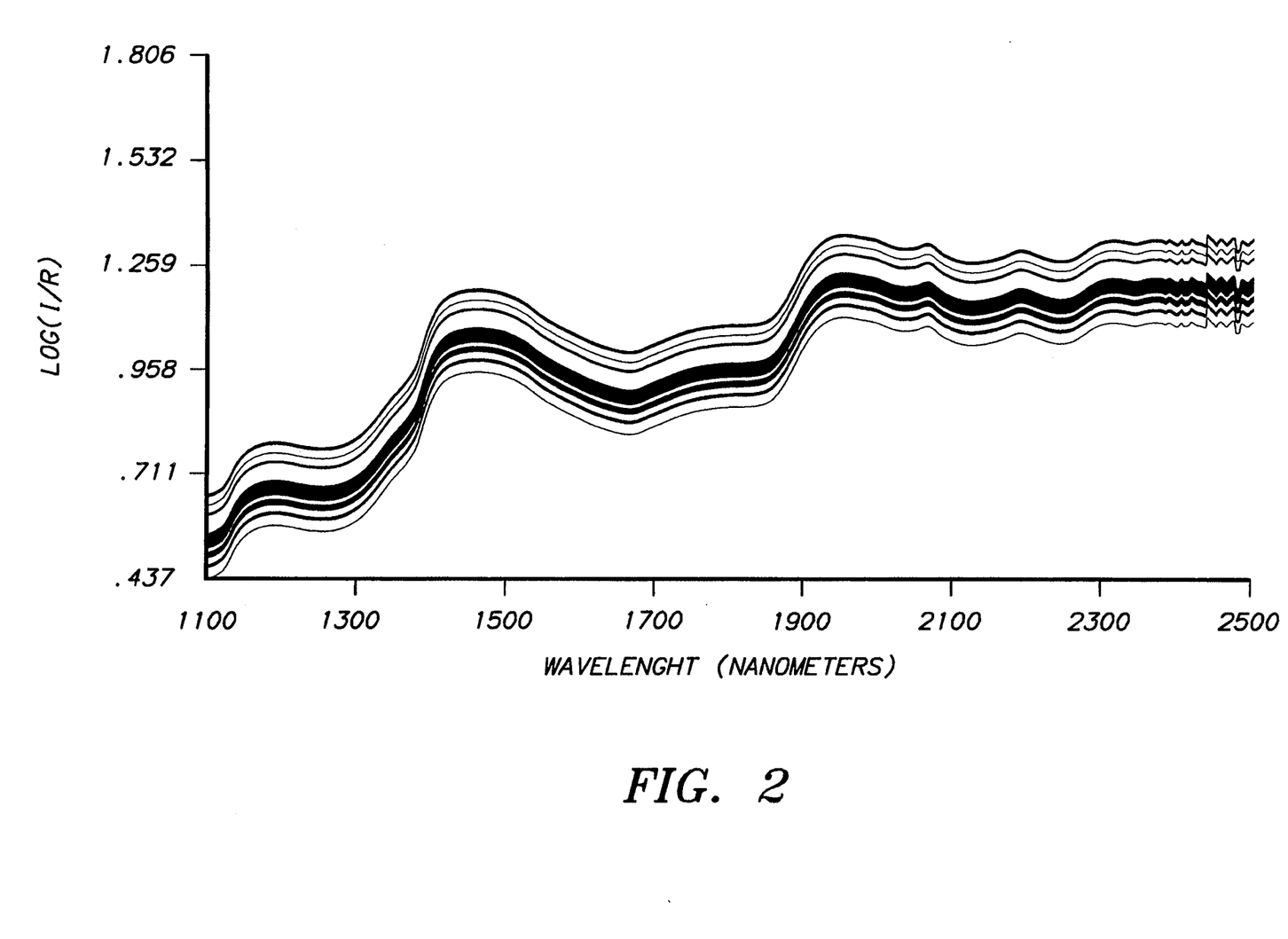
FIG. 2 is a graph presenting 31 spectra of the log of the reciprocal of the reflectance of radiation from a rabbit used as a test subject, i.e., the absorption for the subject, as a function of the wavelength in the near infrared.
Figure 3:
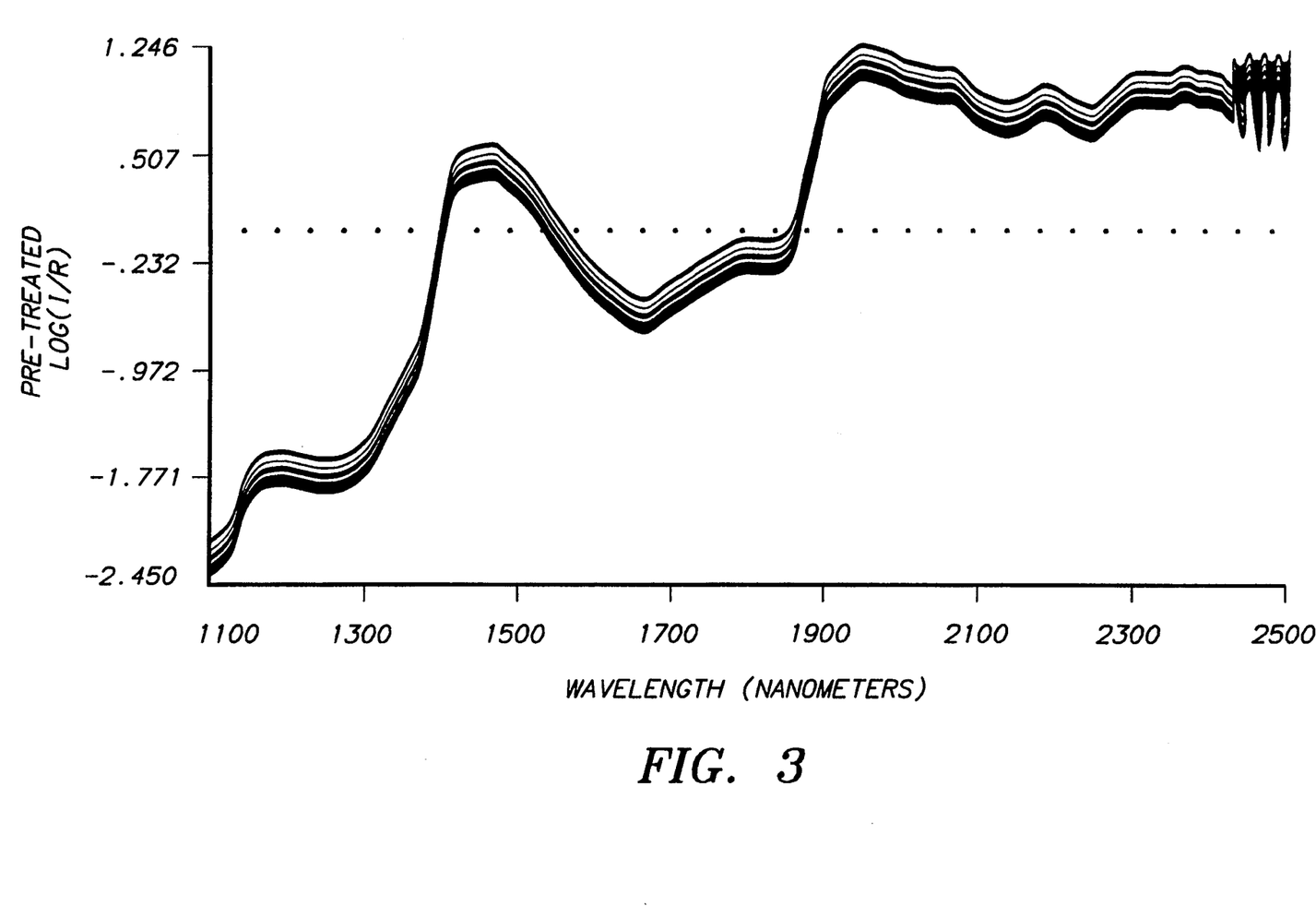
FIG. 3 is a graph presenting the functions shown in FIG. 2 as a function of wavelength after a step of data pretreatment.
Figure 4A:
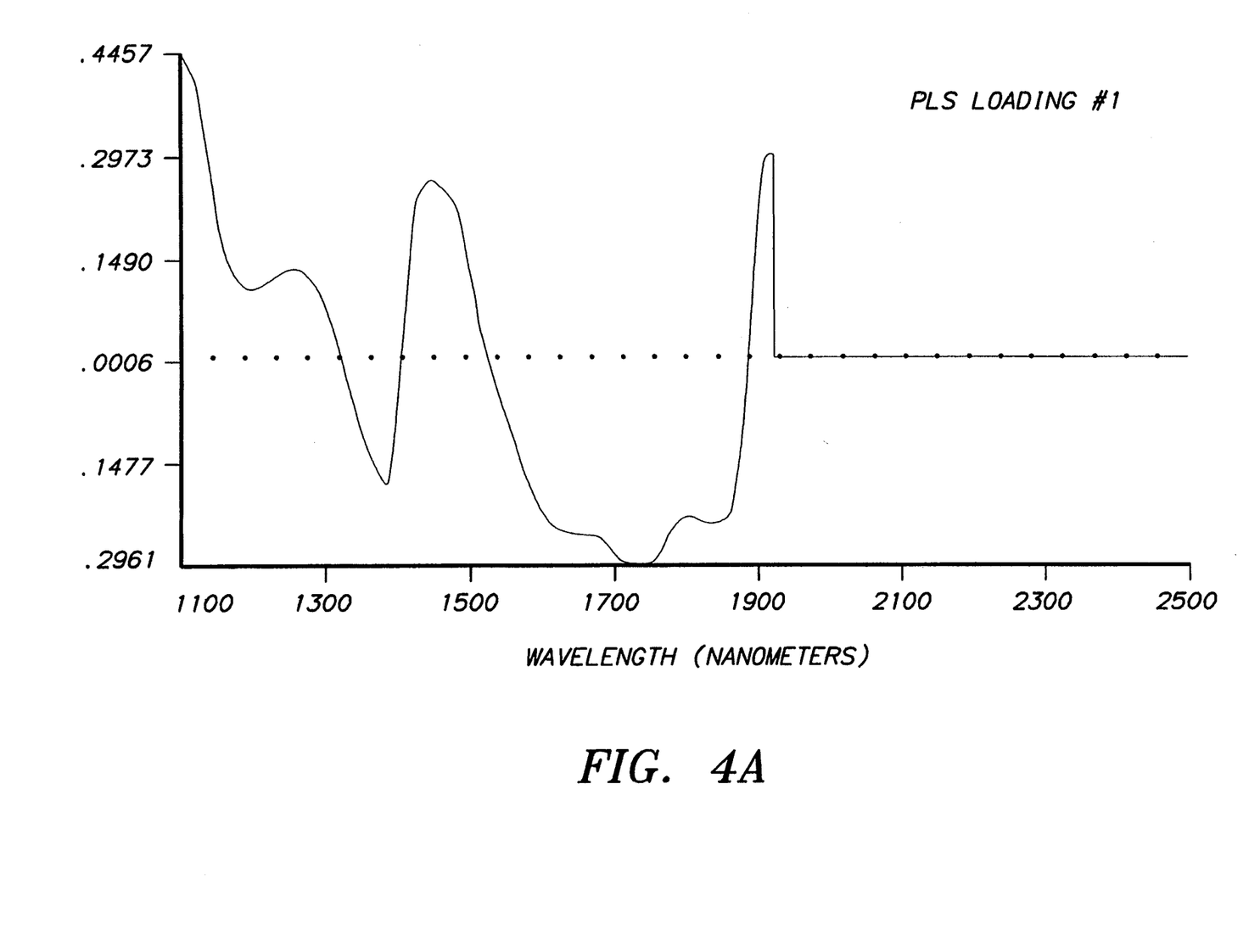
FIG. 4A through 4F are graphs showing six factors in a multivariate analysis model developed using the data of FIG. 2 and 3.
Figure 4B:
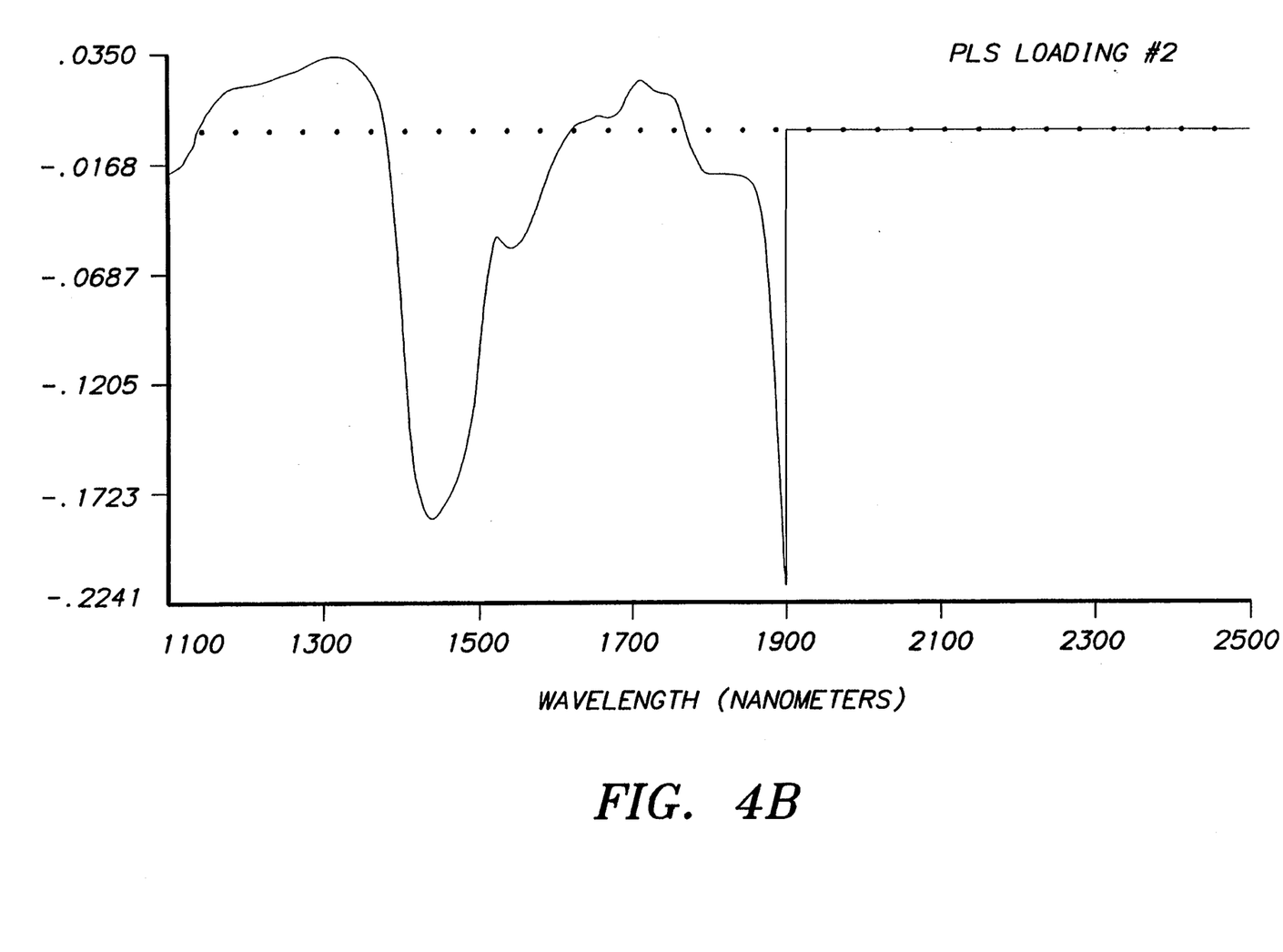
Figure 4C:
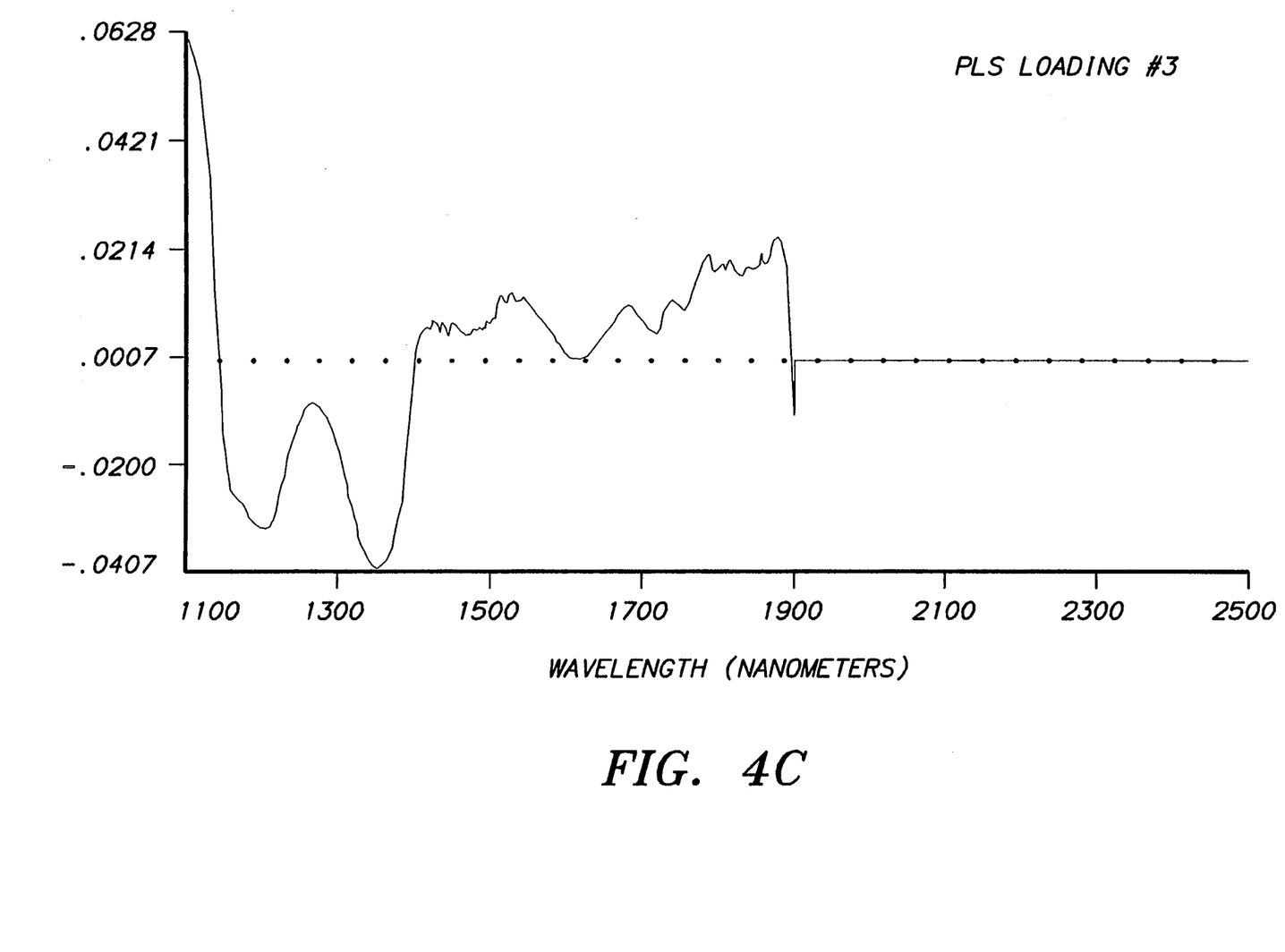
Figure 4D:
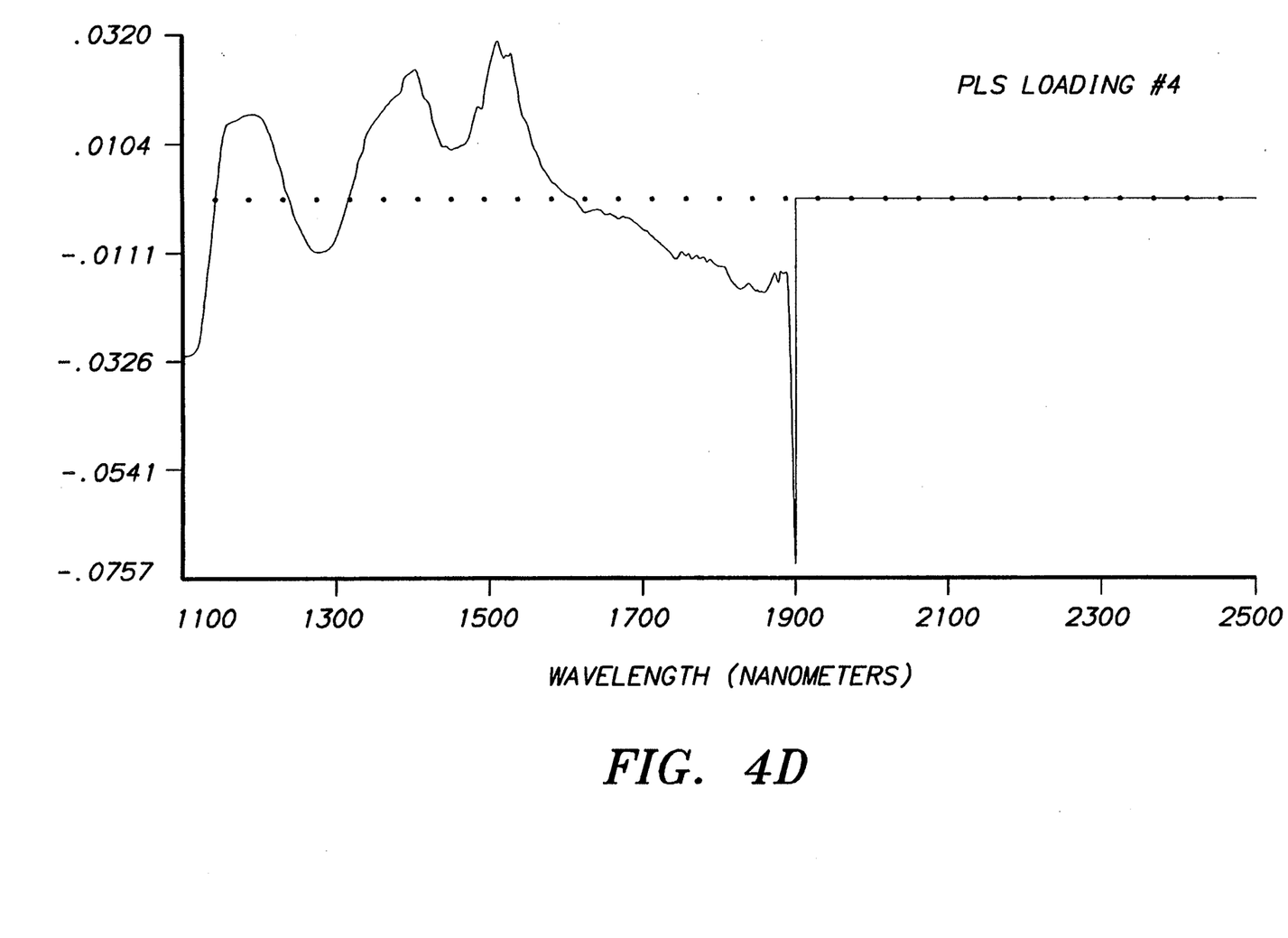
Figure 4E:
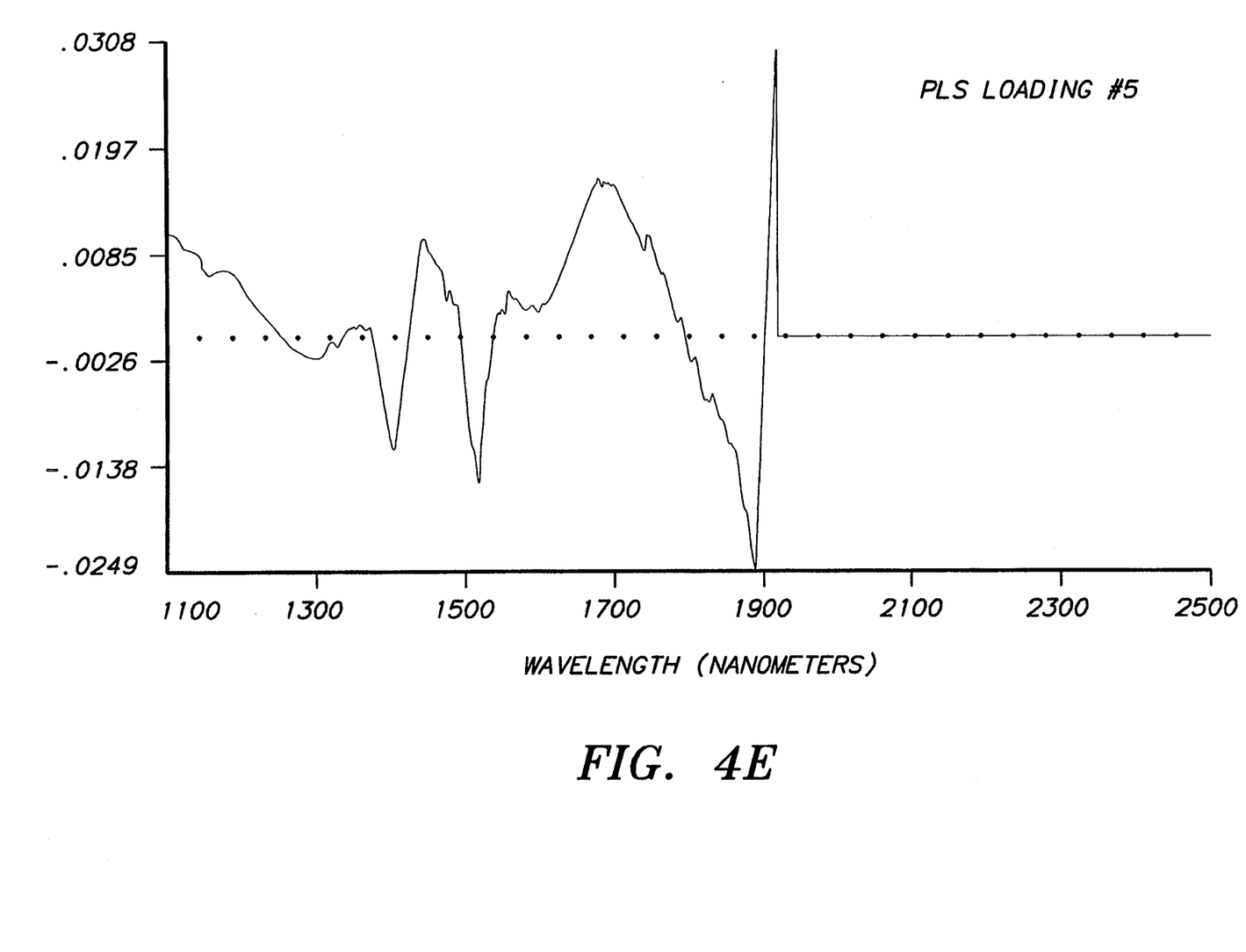
Figure 4F:
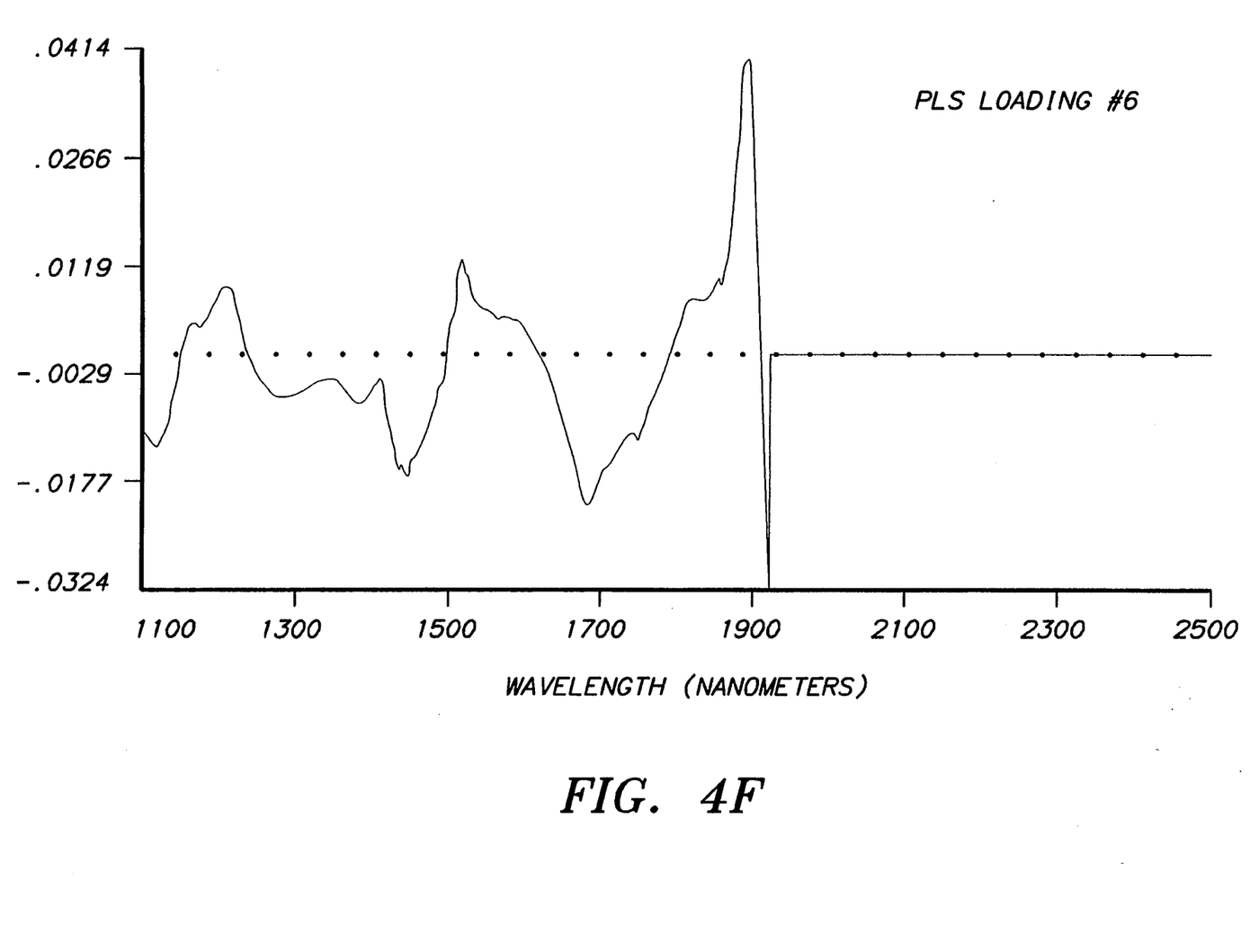

Referring to FIG. 2, there is shown the reflectance intensity vs. wavelength over a range of wavelengths from 1100 nanometers to 2500 nanometers, for 31 readings taken from the rabbit in the calibration set. These data were then pretreated by the data processor, to eliminate the effects of offset and drift. The spectra, after a step of pretreatment, are shown in FIG. 3. As can be seen, the 31 spectra are much closer together than in FIG. 2, indicating the relatively large magnitude of the effects of offset and drift. The method of pretreatment used to obtain the intensity vs. wavelength data of FIG. 3 is that of subtracting the mean of the whole spectrum from each data point in the spectrum and then dividing each data point by the standard deviation of the whole spectrum. This pretreatment step is known as mean-centering and variance scaling. However, it is believed that obtaining the nth derivative, and specifically the second derivative, of the intensity vs. wavelength function, will provide satisfactory results.

The data of FIG. 3 were then reformatted in a conventional manner and employed by a skilled analyst using NIS Systems PLS software, to develop a model. The model contains six factor loadings. Only the data obtained in the range from 1100 to 1900 nanometers were found useful. The six factor loadings are displayed graphically in FIGS. 4A through 4F.

Figure 5:
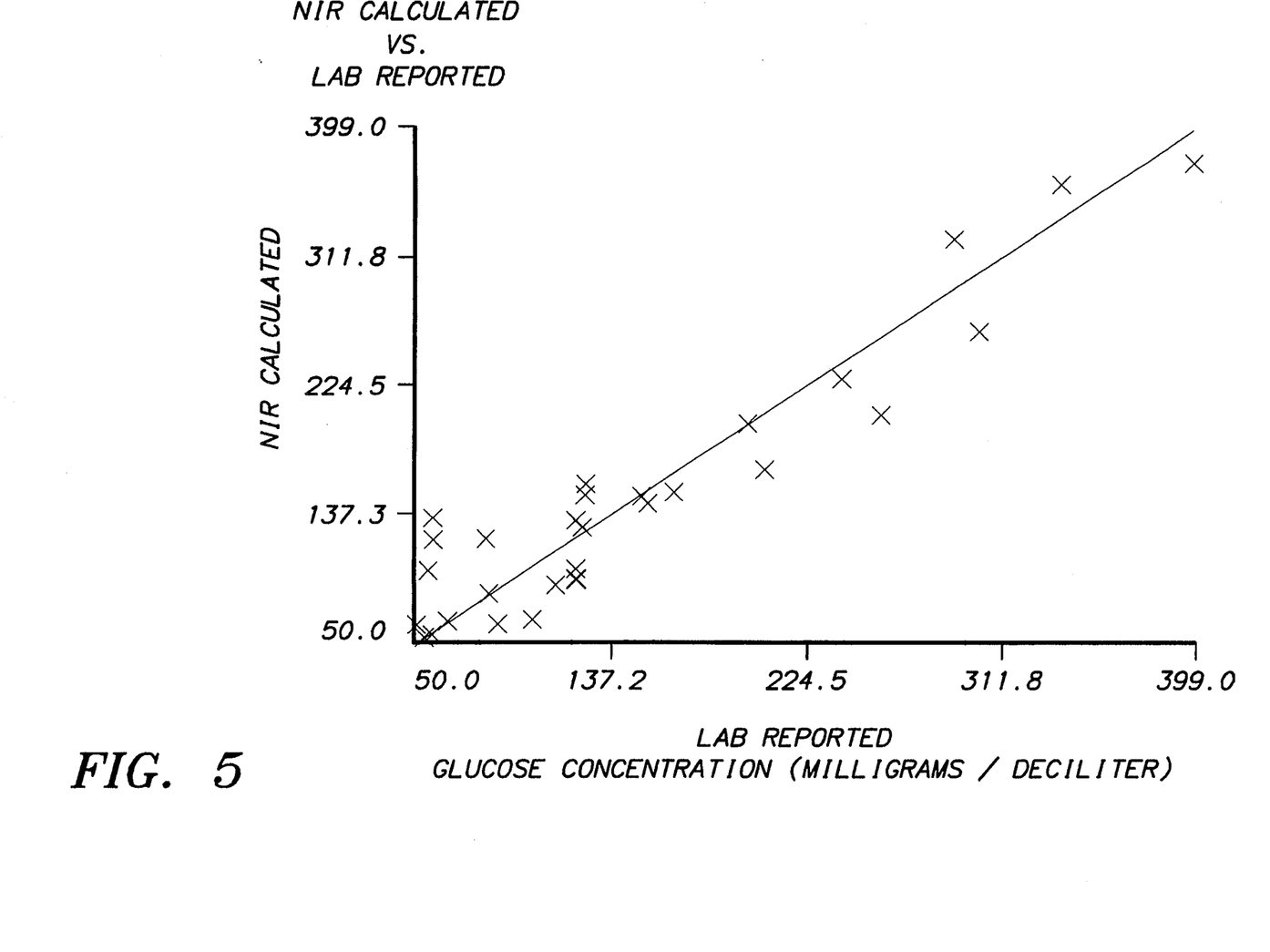
FIG. 5 is a graph in which concentrations of glucose in rabbit blood were determined in vivo and non-invasively in the practice of this invention from the data derived from the graphs shown in FIGS. 2 and 3, using the model of FIGS. 4A–4F, is plotted against the corresponding known concentrations.

This model was then tested against a prediction set of data, obtained simultaneously with the calibration set. The results of this test of the model of FIGS. 4A–4F is shown in FIG. 5. FIG. 5 illustrates calculated glucose concentrations versus actual glucose concentrations. It will be seen that, for higher glucose concentrations, results of very good accuracy were obtained. At lower glucose concentrations, certain readings were very accurate, while others, probably due to the effects of noise, were less accurate.

Figure 6:
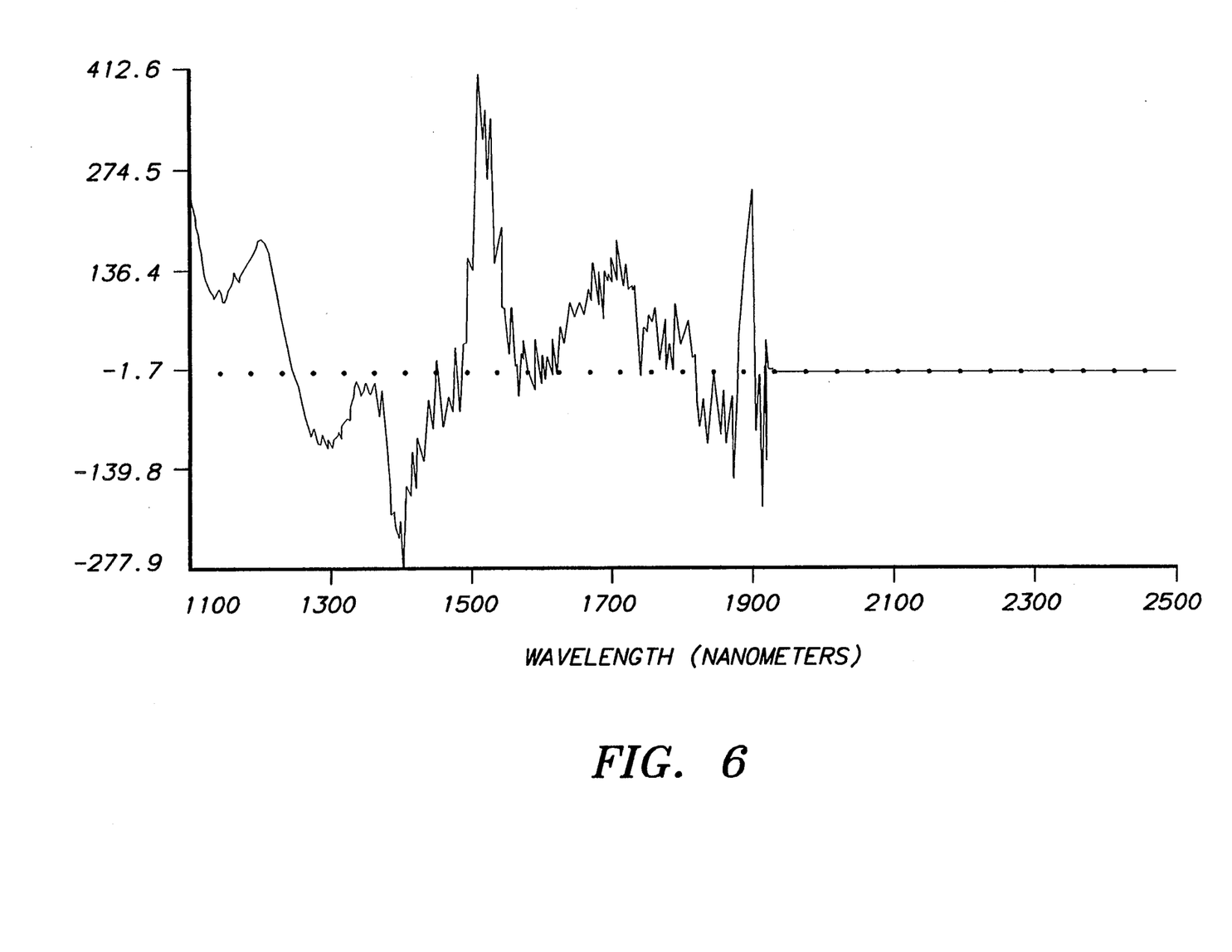
FIG. 6 is a graph in which the model of FIGS. 4A–4F is plotted on a single graph.

Referring to FIG. 6, there is shown the 6-factor PLS model of FIGS. 4A to 4F plotted with respect to wavelength on a single graph, giving weighted averages to each. By multiplying the pretreated absorbance at each wavelength by the value for that wavelength given in FIG. 6, and then adding the products of that calculation, one obtains the concentration value for the analyte. The values shown in FIG. 6 are known as weighting factors or calibration values.

While a preferred embodiment and preferred practice of this invention has been disclosed herein, many modifications thereof are feasible. This invention is not to be restricted except insofar as is necessitated by the spirit of the prior art.

What is claimed is:

1. A method of non-invasive determination of the concentration of at least one analyte in the blood of a mammal, comprising the steps of:
    (a) projecting near infrared radiation on a portion of the body of the mammal, said radiation including a plurality of wavelengths;
    (b) sensing the resulting radiation emitted from said portion of the body;
    (c) deriving from the sensed resulting radiation a first expression for the magnitude of said sensed radiation as a function of wavelength of the sensed radiation;
    (d) pretreating said first expression to minimize the influence of instrument offset and drift to obtain a second expression for the magnitude of said sensed radiation as a function of wavelength; and
    (e) performing multivariate analysis of said second expression to obtain a value for the concentration of said analyte.

2. The method of claim 1, wherein said step of pretreating said first expression comprises the step of obtaining the nth derivative of said first expression.

3. The method of claim 1, wherein said step (e) comprises the step of using the technique of partial least squares.

4. The method of claim 1, wherein said step (e) comprises the step of using the technique of principal component analysis.

5. An apparatus for non-invasive determination of the concentration of at least one analyte in the blood of a mammal, comprising:
    (a) means for projecting near-infrared radiation on a portion of the body of the mammal, said radiation including a plurality of wavelengths;
    (b) means for sensing the resulting radiation emitted from said portion of the body;

(c) means for deriving from the sensed resulting radiation a first expression for the magnitude of said sensed radiation as a function of wavelength of the sensed radiation; and (d) data processing means adapted to (i) pretreat said first expression to minimize the influence of instrument offset and drift to obtain a second expression for the magnitude of said sensed radiation as a function of wavelength and (ii) perform multivariate analysis of said second expression to obtain a value for the concentration of said analyte.

6. The apparatus of claim 5, wherein said data processing means is adapted to pretreat said first expression by obtaining the nth derivative of said first expression.

7. The apparatus of claim 5, wherein said data processing means is adapted to perform multivariate analysis of said second expression using the technique of partial least squares.

8. The apparatus of claim 5, wherein said data processing means is adapted to perform multivariate analysis of said second expression using the technique of principal component analysis.

* * * * *